United States Patent [19]
Hawkins et al.

[11] Patent Number: 5,914,392
[45] Date of Patent: Jun. 22, 1999

[54] ANTIBODIES TO A NOVEL TISSUE INHIBITOR OF METALLOPROTEINASES

[75] Inventors: Phillip R. Hawkins, Mountain View; Lynn E. Murry, Portola Valley, both of Calif.

[73] Assignee: Incyte Pharmaceuticals, Inc., Palo Alto, Calif.

[21] Appl. No.: 09/111,070

[22] Filed: Jul. 7, 1998

Related U.S. Application Data

[62] Division of application No. 08/884,073, Jun. 27, 1997, which is a division of application No. 08/588,163, Jan. 18, 1996, Pat. No. 5,643,752.

[51] Int. Cl.$^6$ ........................ C07K 16/00; A61K 39/395
[52] U.S. Cl. .................................. 530/387.1; 424/130.1; 424/139.1; 424/141.1; 424/146.1
[58] Field of Search ............................. 424/130.1, 141.1, 424/146.1; 530/387.1

[56] References Cited

FOREIGN PATENT DOCUMENTS

WO 96/18725  6/1996  WIPO.

OTHER PUBLICATIONS

Apte, S.S. et al., "The Gene Structure of Tissue Inhibitor of Metalloproteinases (TIMP)–3 and Its Inhibitory Activities Define the Distinct TIMP Gene Family", *J. Biol. Chem.*, 270: 14313–14318 (1995).

Boone, T.C. et al., "cDNA cloning and expression of a metalloproteinase inhibitor related to tissue inhibitor of metalloproteinases," *Proc. Natl. Acad. Sci. USA*, 87: 2800–2804 (1990).

Docherty, A.J.P. et al., "Sequence of human tissue inhibitor of metalloproteinases and its identity to erythroid–potentiating activity", *Nature*, 318: 66–69 (1985).

Freudenstein, J. et al., "mRNA of bovine tissue inhibitor of metalloproteinase: Sequence and expression in bovine ovarian tissue", *Biochem. Biophys. Res. Comm.*, 171: 250–256 (1990).

Gewert, D.R. et al., "Characterization and expression of murine gene homologous to human EPA/TIMP: a virus–induced gene in the mouse", *EMBO J.*, 6: 651–657 (1987).

Horowitz, S. et al., "Hyperoxic Exposure Alters Gene Expression in the Lung," *J. Biol. Chem.*, 264: 7092–7095 (1989).

Howard, E.W. et al., "Preferential Inhibition of 72– and 92–kDa Gelatinases by Tissue Inhibitor of Metalloproteinases–2," *J. Biol. Chem.*, 266: 13070–13075 (1991).

Miyazaki, K. et al., "Purification and Characterization of a Two–chain Form of Tissue Inhibitor of Metalloproteinases (TIMP) Type 2 and a Low Molecular Weight TIMP–like Protein," *J. Biol. Chem.*, 268: 14387–14393 (1993).

Pavloff, N. et al., "A New Inhibitor of Metalloproteinases from Chicken: ChIMP–3" *J. Biol. Chem.*, 267: 17321–17326 (1992).

Stetler–Stevenson, W.G. et al., "Tissue Inhibitor of Metalloproteinases–2 (TIMP–2) mRNA Expression in Tumor Cell Lines and Human Tumor Tissues," *J. Biol. Chem.*, 265: 13933–13938 (1990).

Wilde, C.G. et al., "Cloning and Characterization of Human Tissue Inhibitor of Metalloproteinases–3", *DNA Cell Biol.*, 13: 711–718 (1994).

Wick, M. et al., "A Novel Member of Human Tissue Inhibitor of Metalloproteinases (TIMP) Gene Family is Regulated during $G_1$ Progression, Mitogenic Stimulation, Differentiation, and Senescence" *J. Biol. Chem.*, 269: 18953–18960 (1994).

Cook, T. F. et al., "Cloning and Regulation of Rat Tissue Inhibitor of Metalloproteinases–2 in Osteoblastic Cells", *Archives of Biochemistry and Biophysics*, 311:313–320 (1994).

*Primary Examiner*—George C. Elliott
*Assistant Examiner*—Andrew Wang
*Attorney, Agent, or Firm*—Incyte Pharmaceuticals, Inc.

[57] ABSTRACT

The present invention provides a nucleic acid sequence which identifies and encodes a novel tissue inhibitor of metalloproteinases (TIMP-4) which was isolated from cells of human uterus. The invention provides for TIMP-4 antisense molecules and genetically engineered expression vectors and host cells comprising nucleic acid sequence encoding TIMP-4. The invention also provides for purified TIMP-4; antibodies, antagonists and inhibitors which specifically bind TIMP-4; and pharmaceutical compositions and methods of treatment based on TIMP-4, its antagonists and inhibitors. The invention provides for diagnostic assays which utilize diagnostic compositions comprising nucleic acid sequences encoding to TIMP-4, or complements thereof, and antibodies which specifically bind to TIMP-4.

1 Claim, 6 Drawing Sheets

FIGURE 1A

```
109 A G K L Q D G L L H I T T C S F V A P W N S L S L A Q R R G    TIMP-1
118 G Q V L S D G K V F I H L C N Y I E P W E D L S L V Q R E S    TIMP-4

139 F T K T Y T V G C E E C T V F P C L S I P C K L Q S G T H C    TIMP-1
148 L N H H Y H L N C G - C Q I T T C Y T V P C T I S A P N E C    TIMP-4

169 L W T D Q L L Q G S E K G F Q S R H L A C L P R E P G L C T    TIMP-1
177 L W T D W L L E R K L Y G Y Q A Q H Y V C M K H V D G T C S    TIMP-4

199 W - - - Q S L R S Q I - - - - - A                              TIMP-1
207 W Y R G H L P L R K E F V D I V Q P                            TIMP-4
```

FIGURE 1B

1    MPGSPRPAPSWLLLRLLALLRPPGLGEACSSCAPAHPQQHICHSALVIRAKISSEKVVPASAD.PADTEKMLRYEIKQIKMFK
      -|---|---||-|---|||       -|||--|-|||---|||--|||---|---   -|----|||||||
1    MGAAARTLRLALGLLLLATLLRP...ADACSCSPVHPQQAFCNADVVIRAKAVSEKEVDSGNDIYGNPIKRIQYEIKQIKMFK

83   GFEKVKDVQYIYTPFDSSLCGVKLFANSQKQYLLTGQVLSDGKVFIHLCNYIEPWEDLSLVQRESLNHHYHLNCGCQITTCYT
     |--|   ||--|---|||-|       -||--|-||--||-|--||-||--|-||---|-||--|||-||-|--|---
81   GPE..KDIEFIYTAPSSAVCGVSLDVGGKKEYLIAGKAEGDGKMHITLCDFIVPWDTLSTTQKKSLNHRYQMGCECKITRCPM

166  VPCTISAPNECLWTDWLLERKLYGYQAQHYVCMKHVDGTCSWYRGHLPLRKEFVDIVQP*
     -||-|---|---||---|---|-|---|---|-||--||--||---||-||---|--|
162  IPCYISSPDECLWMDWVTEKNINGHQAKFFACIKRSDGSCAWYRGAAPPKQEFLDIEDP.

FIGURE 2

```
  1   MPGSPRPAPSWVLLLRLLALLRPPGLG....EACSCAPAHPQQHICHSALVIRAKISSEKVVPASADPADTEKMLRYEIKQIK
        ---|-|--||------||    |||-|-||--|-|-|||-----|||| ---|-|     |-|-|||-|--
  1   ..........MTPWLGLIVLLGSWSLGDWGAEACTCSPSHPQDAFCNSDIVIRAKVVGKKLV..KEGPFGT...LVYTIKQMK

80   MFKGFEKVKDVQYIYTPFDSSLCGVKLEANSQKQYLLTGQVLSDGKVFIHLCNYIEPWEDLSLVQRESLNHHYHLNCGCQITT
        |-|--|||--|---||||-|----||||-|-|||||-|  -||-|--|-|-|||-|-|||-||-|||--|--
 69   MYRGFTKMPHVQYIHTEASESLCGLKLEVN.KYQYLLTGRV.YDGKMYTGLCNFVERWDQLTLSQRKGLNYRYHLGCNCKIKS

163   CYTVPCTISAPNECLWTDWLLERKLYGYQAQHYVCMKHVDGTCSWYRGHLPLRKEFVDIVQP*
       ||--||-----||||||-||--||---|--||-||-|-||-||||-|||||--|-|---||
150   CYYLPCFVTSKNECLWTDMLSNFGYPGYQSKHYACIRQKGGYCSWYRGWAPPDKSIINATDP*
```

FIGURE 3

```
                                   9              18               27              36              45              54
5'  ATG  CCT  GGG  AGC  CCT  CGG  CCC  GCG  CCA  AGC  TGG  GTG  CTG  TTG  CTG  CGG  CTG
    M    P    G    S    P    R    P    A    P    S    W    V    L    L    L    R    L 63              72               81              90              99             108
    GCG  TTG  CTG  CGG  CCC  CCG  GGG  CTG  GGT  GAG  GCA  TGC  AGC  TGC  GCC  CCG  GCG  CAC
    A    L    L    R    P    P    G    L    G    E    A    C    S    C    A    P    A    H 117             126              135             144             153             162
    CCT  CAG  CAG  CAC  ATC  TGC  CAC  TCG  GCA  CTT  GTG  ATT  CGG  GCC  AAA  ATC  TCC  AGT
    P    Q    Q    H    I    C    H    S    A    L    V    I    R    A    K    I    S    S 171             180              189             198             207             216
    GAG  AAG  GTA  GTT  CCG  GCC  AGT  GCA  GAC  CCT  GCT  GAC  ACT  GAA  AAA  ATG  CTC  CGG
    E    K    V    V    P    A    S    A    D    P    A    D    T    E    K    M    L    R 225             234              243             252             261             270
    TAT  GAA  ATC  AAA  CAG  ATA  AAG  ATG  TTC  AAA  GGG  TTT  GAG  AAA  GTC  AAG  GAT  GTT
    Y    E    I    K    Q    I    K    M    F    K    G    F    E    K    V    K    D    V 279             288              297             306             315             324
    CAA  TAT  ATC  TAT  ACG  CCT  TTT  GAC  TCT  TCC  CTC  TGT  GGT  GTG  AAA  CTA  GAA  GCC
    Q    Y    I    Y    T    P    F    D    S    S    L    C    G    V    K    L    E    A
```

FIGURE 4A

```
            333         342         351    360    369    378
AAC AGC CAG AAG CAG TAT CTC TTG ACT GGT CAG CTC AGT GAT GGA AAA GTC
 N   S   Q   K   Q   Y   L   L   T   G   Q   L   S   D   G   K   V 387         396         405    414    423    432
TTC ATC CAT CTG TGC AAC TAC ATC GAG CCC TGG GAG GAC CTG TCC TTG GTG CAG
 F   I   H   L   C   N   Y   I   E   P   W   E   D   L   S   L   V   Q 441         450         459    468    477    486
AGG GAA AGT CTG AAT CAT CAC TAC CAT CTG AAC TGT GGC CAA ATC ACC ACC
 R   E   S   L   N   H   H   Y   H   L   N   C   G   Q   I   T   T 495         504         513    522    531    540
TGC TAC ACA GTA CCC TGT ACC ATC TCG GCC CCT AAC GAG TGC CTC TGG ACA GAC
 C   Y   T   V   P   C   T   I   S   A   P   N   E   C   L   W   T   D 549         558         567    576    585    594
TGG CTG GAA CGA AAG CTC TAT GGT TAC CAG GCT CAG CAT TAT CTC TGT ATG
 W   L   E   R   K   L   Y   G   Y   Q   A   Q   H   Y   L   C   M 603         612         621    630    639    648
AAG CAT GTT GAC GGC ACC TGC AGC TGG TAC CGG GGC CAC CTG CCT CTC AGG AAG
 K   H   V   D   G   T   C   S   W   Y   R   G   H   L   P   L   R   K 657         666         675
GAG TTT GTT GAC ATC GTT CAG CCC TAG 3'
 E   F   V   D   I   V   Q   P   *
```

FIGURE 4B

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: METALLOPROTEINASES
        (B) CLONE: 589345

(xi) SEQUENCE DESCRIPTION: SEQ ID NO:1:

```
ATGCCTGGGA GCCCTCGGCC CGCGCCAAGC TGGGTGCTGT TGCTGCGGCT GCTGGCGTTG      60

CTGCGGCCCC CGGGGCTGGG TGAGGCATGC AGCTGCGCCC GGCGCACCC TCAGCAGCAC      120

ATCTGCCACT CGGCACTTGT GATTCGGGCC AAAATCTCCA GTGAGAAGGT AGTTCCGGCC      180

AGTGCAGACC CTGCTGACAC TGAAAAAATG CTCCGGTATG AAATCAAACA GATAAAGATG     240

TTCAAAGGGT TTGAGAAAGT CAAGGATGTT CAATATATCT ATACGCCTTT TGACTCTTCC    300

CTCTGTGGTG TGAAACTAGA AGCCAACAGC CAGAAGCAGT ATCTCTTGAC TGGTCAGGTC    360

CTCAGTGATG GAAAAGTCTT CATCCATCTG TGCAACTACA TCGAGCCCTG GGAGGACCTG    420

TCCTTGGTGC AGAGGGAAAG TCTGAATCAT CACTACCATC TGAACTGTGG CTGCCAAATC    480

ACCACCTGCT ACACAGTACC CTGTACCATC TCGGCCCCTA ACGAGTGCCT CTGGACAGAC    540

TGGCTGTTGG AACGAAAGCT CTATGGTTAC CAGGCTCAGC ATTATGTCTG TATGAAGCAT    600

GTTGACGGCA CCTGCAGCTG GTACCGGGGC CACCTGCCTC TCAGGAAGGA GTTTGTTGAC    660

ATCGTTCAGC CCTAG                                                    675
```

(2) INFORMATION FOR SEQ ID NO:2:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: METALLOPROTEINASES
        (B) CLONE: 589345

(xi) SEQUENCE DESCRIPTION: SEQ ID NO:2:

```
Met Pro Gly Ser Pro Arg Pro Ala Pro Ser Trp Val Leu Leu Leu Arg
 1               5                  10                  15

Leu Leu Ala Leu Leu Arg Pro Pro Gly Leu Gly Glu Ala Cys Ser Cys
            20                  25                  30

Ala Pro Ala His Pro Gln Gln His Ile Cys His Ser Ala Leu Val Ile
        35                  40                  45

Arg Ala Lys Ile Ser Ser Glu Lys Val Val Pro Ala Ser Ala Asp Pro
50                  55                  60

Ala Asp Thr Glu Lys Met Leu Arg Tyr Glu Ile Lys Gln Ile Lys Met
65                  70                  75                  80

Phe Lys Gly Phe Glu Lys Val Lys Asp Val Gln Tyr Ile Tyr Thr Pro
                85                  90                  95

Phe Asp Ser Ser Leu Cys Gly Val Lys Leu Glu Ala Asn Ser Gln Lys
               100                 105                 110
```

```
Gln Tyr Leu Leu Thr Gly Gln Val Leu Ser Asp Gly Lys Val Phe Ile
            115                 120                 125

His Leu Cys Asn Tyr Ile Glu Pro Trp Glu Asp Leu Ser Leu Val Gln
    130                 135                 140

Arg Glu Ser Leu Asn His His Tyr His Leu Asn Cys Gly Cys Gln Ile
145                 150                 155                 160

Thr Thr Cys Tyr Thr Val Pro Cys Thr Ile Ser Ala Pro Asn Glu Cys
                165                 170                 175

Leu Trp Thr Asp Trp Leu Leu Glu Arg Lys Leu Tyr Gly Tyr Gln Ala
            180                 185                 190

Gln His Tyr Val Cys Met Lys His Val Asp Gly Thr Cys Ser Trp Tyr
        195                 200                 205

Arg Gly His Leu Pro Leu Arg Lys Glu Phe Val Asp Ile Val Gln Pro
210                 215                 220
```

(2) INFORMATION FOR SEQ ID NO:3:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: METALLOPROTEINASES
        (B) CLONE: TIMP-2

(xi) SEQUENCE DESCRIPTION: SEQ ID NO:3:

```
Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys
        35                  40                  45

Ala Val Ser Glu Lys Glu Val Asp Ser Gly Asn Asp Ile Tyr Gly Asn
50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
        115                 120                 125

Phe Ile Val Pro Trp Asp Thr Leu Ser Thr Gln Lys Lys Ser Leu
130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
        195                 200                 205

Pro Pro Lys Gln Glu Phe Leu Asp Ile Glu Asp Pro
210                 215                 220
```

(2) INFORMATION FOR SEQ ID NO:4:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: METALLOPROTEINASES
        (B) CLONE: TIMP-3

(xi) SEQUENCE DESCRIPTION: SEQ ID NO:4:

```
Met Thr Pro Trp Leu Gly Leu Ile Val Leu Leu Gly Ser Trp Ser Leu
  1               5                  10                  15

Gly Asp Trp Gly Ala Glu Ala Cys Thr Cys Ser Pro Ser His Pro Gln
             20                  25                  30

Asp Ala Phe Cys Asn Ser Asp Ile Val Ile Arg Ala Lys Val Val Gly
             35                  40                  45

Lys Lys Leu Val Lys Glu Gly Pro Phe Gly Thr Leu Val Tyr Thr Ile
 50                  55                  60

Lys Gln Met Lys Met Tyr Arg Gly Phe Thr Lys Met Pro His Val Gln
 65                  70                  75                  80

Tyr Ile His Thr Glu Ala Ser Glu Ser Leu Cys Gly Leu Lys Leu Glu
             85                  90                  95

Val Asn Lys Tyr Gln Tyr Leu Leu Thr Gly Arg Val Tyr Asp Gly Lys
                100                 105                 110

Met Tyr Thr Gly Leu Cys Asn Phe Val Glu Arg Trp Asp Gln Leu Thr
            115                 120                 125

Leu Ser Gln Arg Lys Gly Leu Asn Tyr Arg Tyr His Leu Gly Cys Asn
130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
            195                 200                 205

Thr Asp Pro
   210
```

(2) INFORMATION FOR SEQ ID NO:5:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: METALLOPROTEINASES
        (B) CLONE: TIMP-1

(xi) SEQUENCE DESCRIPTION: SEQ ID NO:5:

```
Met Ala Pro Phe Glu Pro Leu Ala Ser Gly Ile Leu Leu Leu Leu Trp
  1               5                  10                  15
```

-continued

```
Leu Ile Ala Pro Ser Arg Ala Cys Thr Cys Val Pro Pro His Pro Gln
         20                  25                  30

Thr Ala Phe Cys Asn Ser Asp Leu Val Ile Arg Ala Lys Phe Val Gly
         35                  40                  45

Thr Pro Glu Val Asn Gln Thr Thr Leu Tyr Gln Arg Tyr Glu Ile Lys
 50                      55                  60

Met Thr Lys Met Tyr Lys Gly Phe Gln Ala Leu Gly Asp Ala Ala Asp
 65                  70                  75                  80

Ile Arg Phe Val Tyr Thr Pro Ala Met Glu Ser Val Cys Gly Tyr Phe
                 85                  90                  95

His Arg Ser His Asn Arg Ser Glu Glu Phe Leu Ile Ala Gly Lys Leu
             100                 105                 110

Gln Asp Gly Leu Leu His Ile Thr Thr Cys Ser Phe Val Ala Pro Trp
         115                 120                 125

Asn Ser Leu Ser Leu Ala Gln Arg Arg Gly Phe Thr Lys Thr Tyr Thr
 130                 135                 140

Val Gly Cys Glu Glu Cys Thr Val Phe Pro Cys Leu Ser Ile Pro Cys
 145             150                 155                 160

Lys Leu Gln Ser Gly Thr His Cys Leu Trp Thr Asp Gln Leu Leu Gln
             165                 170                 175

Gly Ser Glu Lys Gly Phe Gln Ser Arg His Leu Ala Cys Leu Pro Arg
             180                 185                 190

Glu Pro Gly Leu Cys Thr Trp Gln Ser Leu Arg Ser Gln Ile Ala
             195                 200                 205
```

ANTIBODIES TO A NOVEL TISSUE INHIBITOR OF METALLOPROTEINASES

This application is a divisional application of U.S. application Ser. No. 08/884,073, filed Jun. 27, 1997, which is a divisional application of U.S. application Ser. No. 08/588,163, filed Jan. 18, 1996, now U.S. Pat. No. 5,643,752.

FIELD OF THE INVENTION

The present invention relates to nucleic acid and amino acid sequences of a novel metalloproteinase inhibitor from human uterus and to the use of these sequences in the diagnosis, study, prevention and treatment of disease.

BACKGROUND OF THE INVENTION

Tissue inhibitors of metalloproteinases (TIMPs) inhibit metalloproteinases, a multigene family of endopeptide hydrolases. The metalloproteinases are secreted by connective tissue and hematopoietic cells, use $Zn^{++}$ or $Ca^{++}$ for catalysis, and may be inactivated by metal chelators as well as TIMP molecules.

The matrix metalloproteinases (MMPs) participate in a variety of biologically important processes including the degradation of many structural components of tissues, particularly the extracellular matrix (ECM). This ability is desirable in processes where destruction of existing tissues is necessary, eg, in embryo implantation (Reponen P. et al. (1995) Dev Dyn 202:388–96), embryogenesis, and tissue remodeling. Metalloproteinases have also been implicated in processes where their activity is more specifically directed, such as in the movement of cells through tissues. Some of these molecules and their known substrates as reviewed in Murphy G. and A. J. P. Docherty (1992; Am J Respir Cell Mol Biol 120–125) are summarized below:

| MMP-1 | Interstitial collagenase | Fibrillar Type X Collagens; Gelatin; Proteoglycan |
| MMP-2 | Gelatinase A | Collagens IV, V, VII, X, XI; Elastin |
| MMP-3 | Stromelysin-1 | Proteoglycan; Collagens II, IV, IX, X, XI; Fibronectin; Procollagen; Laminin; Gelatin; Collagenase; Gelatinase B |
| MMP-7 | Matrilysin | Proteoglycan; Collagens II, IV, IX, X, XI; Fibronectin; Procollagen; Laminin; Gelatin; Collagenase; Gelatinase B; Elastin |
| MMP-8 | Neutrophil collagenase | Fibrillar Collagens; Gelatin, Proteoglycans |
| MMP-9 | Gelatinase B | Collagens IV, V, VII, X, XI; Elastin |
| MMP-10 | Stromelysin-2 | Proteoglycan; Collagens II, IV, IX, X, XI; Fibronectin; Procollagen; Laminin; Gelatin; Collagenase; Gelatinase B |

Metalloproteinases also inactivate several members of a class of serine protease inhibitors known as serpins. The inactivation of the serpins such as alpha-1 protease inhibitor allows serine proteases to destroy a variety of biologically important, non-ECM, molecules such as alpha-1 antitrypsin (Sorsa T. et al. (1993) Agents Actions Suppl 39:225–9). Therefore, controlling the activity of the metalloproteinases can have indirect effects on the activity of a range of other potent proteases.

It is, however, the MMPs which play the most important roles in pathological processes. In rheumatoid and other forms of arthritis, proteolysis of extracellular matrix components by MMPs is a major cause of cartilage and synovial tissue destruction (Firestein G. S. (1992) Curr Opin Rheumatol 4:348–54). Similarly, the activity of elastinolytic MMPs secreted by mononuclear phagocytes has been implicated in the destruction of alveolar structure in pulmonary emphysema (Shapiro S. D. (1994) Am J Respir Crit Care Med).

MMPs are also associated with tumor metastasis. In order to colonize secondary sites, the primary tumor cells must both enter and exit the vascular system. This movement through tissues and the endothelial basement membrane is aided by the activity of metalloproteinases secreted by the tumor cells. In addition, the degradation of normal extracellular matrix structure is critical for angiogenesis as well as tumor cell migration (Ray J. M. and Stetler-Stevenson W. G. (1994) Eur Respir J 7:2062–72; Mignatti P. and Rifkin D. B. (1993) Physiol Rev 73:161–95).

MMPs have also been implicated in periodontal disease where inflammation of the periodontium leads to connective tissue degradation and eventually to tooth loss. Tissue degradation is largely mediated by neutrophils which are attracted to sites of inflammation and secrete the MMPs believed to play a major role in tissue destruction (Sodek J. and Overall C. M. (1992) Matrix Suppl 1:352–62). MMPs are also involved in corneal ulcer formation following alkali burns and bacterial inflammation (Wentworth J. S. et al. (1992) 33:2174–9; Burns F. R. et al. (1992) Matrix Suppl 1:317–318).

MMPs participate in both normal and abnormal bone resorption. Collagenase produced by osteoblasts degrades collagen on the surface of the bone and affords osteoclasts access to underlying mineralized bone. The osteoclasts utilize MMPs and other proteases to resorb bone. When catabolism exceeds deposition, the resulting imbalance can lead to demineralization of the bone and osteoporosis or osteoarthritis (Hembry R. M. et at (1995) Ann Rheum Dis 54:25–32; Everts V. et al. (1992) J Cell Physiol 150:221–231; Vaes G. et al. (1992) Matrix Suppl 1:383–388). Even though TIMPs are expressed in osteoarthritic joints, the amount of inhibitory activity does not compensate for the amounts of MMPs carrying out degradation.

The involvement of MMPs in a wide range of pathological conditions suggests that natural inhibitors of MMPs, such as TIMPs, would be therapeutically useful for treatment of pathological conditions associated with excessive expression of MMPs.

TIMP Molecules

The nucleotide and amino acid sequences of three human TIMPs have been previously characterized and named TIMP-1 (Docherty A. J. P. et al. (1985) Nature 318:66–69), TIMP-2 (Boone T. C. et al. (1990) Proc Natl Acad Sci 87:2800–2804; Stetler-Stevenson W. G. et al. (1990) J Biol Chem 265: 13933–38), and TIMP-3 (Wilde C. G. et al. (1994) DNA Cell Biol 13:711–18). These proteins are classified as TIMPs based on their ability to inhibit metalloproteinases, structural similarity to each other, the 12 cysteines which form disulfide bonds important in secondary structure, and the presence of the VIRAK motif which interacts with the metal ion of the metalloproteinases.

Although human TIMPs inhibit a variety of metalloproteinases, the expression and specific activity of individual TIMPs do differ. TIMP-1, a 30 kD protein, is the most commonly expressed molecule and contains two asparagine residues which act as carbohydrate binding sites, one in loop 1 and one in loop 2(Murphy and Docherty, supra). In addition, a truncated form of TIMP-1 which contains only the first three loops of the molecule is able to inhibit MMPs. Although TIMP-1 is a better inhibitor of interstitial collagenase than TIMP-2 (Howard E. W. et al. (1991) J Biol Chem 266:13070–75), the 23 kD TIMP-2 molecule is the most effective inhibitor of gelatinases A and B. TIMP-3 is a 21 kD protein which inhibits collagenase 1, stromelysin, and gelatinases A and B (Apte S. S. et al. (1995) J Biol Chem 270:14313–18) and may be induced by mitogens (Wick et al. (1994) J Biol Chem 269:18953–60).

There have been reports of other inhibitors of metalloproteinases (IMPs) with physical characteristics different from those of the known TIMPs. In some cases, these activities result from alternate forms of the known TIMPs. For example, one IMP present in the conditioned media of a human bladder carcinoma was identified as a partially glycosylated form of TIMP-1, and another, as a partially processed/degraded form of TIMP-2 (Miyazaki K. et al. (1993) J Biol Chem 268:14387–93). Additional reports have described sources and characteristics of IMP activity, but active molecules have not been identified (Apodaca G. et al. (1990) Cancer Research 50:2322–29).

TIMPs which have been cloned from other species include bovine TIMP-1 (Freudenstein R. et al. (1990) Biochem Biophys Res Comm 171:250–256) and TIMP-2 (Boone T. C. et al. (1990) Proc Natl Acad Sci 87:2800–2804); murine TIMP-1 (Gewert D. R. et al. (1987) EMBO J 6:651–657); rabbit TIMP-1 (Horowitz S. et al. (1989) J Biol Chem 264:7092–7095); and chicken TIMP-3 (Pavloff N. et al. (1992) J Biol Chem 267:17321–6).

SUMMARY

The present invention relates to a novel tissue inhibitor of metalloproteinases, TIMP-4, whose nucleic acid sequence was identified among the polynucleotides of a human uterus library and to the use of the nucleic acid and amino acid sequences of TIMP-4 in the study, diagnosis, prevention and treatment of disease.

The novel polynucleotide encoding TIMP-4 was first identified within Incyte Clone No. 589345 through a computer generated search for nucleotide sequence alignments. The clone was resequenced, and the coding region determined. The nucleotide sequence encodes a protein of 224 amino acids including the 5' signal sequence of 29 residues, $M_1$ through $A_{29}$ of SEQ ID NO:2. Other significant features of the protein include the presence of the VIRAK motif at amino acid residues 47 through 51 of SEQ ID NO:2 and the 12 cysteine residues characteristic of known TIMPs. The present invention is based, in part, on the facts that TIMP-4 is more closely related to TIMP-2 than to the other TIMPs and that both TIMP-4 and TIMP-2 have been found in female reproductive tissues.

The use of TIMP-4, and of the nucleic acid sequences which encode it, is based on the amino acid and structural homologies between TIMP-4 and the other known TIMPs and on the ability of the known TIMPS to inhibit the activities of MMPs. The timing of and amount of expression of MMPs and TIMPs are implicated in metastasis of neoplastic cells, angiogenesis and growth of tumors such as cervical, uterine, pancreatic, colon or intestinal carcinomas, pregnancy, osteoarthritis, osteoporosis, pulmonary emphysema, periodontal disease, rheumatoid arthritis, corneal or diabetic ulcers or ulcers/lesions caused by microorganisms.

The TIMP-4 polynucleotide sequence, oligonucleotides, fragments, portions or antisense molecules thereof, may be used in diagnostic assays to detect and quantify levels of TIMP-4 mRNA in cells and tissues. For example, TIMP-4 polynucleotides, or fragments thereof, may be used in hybridization assays of bodily fluids or biopsied tissues to detect the level of TIMP-4 expression.

The present invention also relates, in part, to an expression vector and host cells comprising nucleic acids encoding TIMP-4. Such transfected host cells are useful for the production and recovery of TIMP-4. The present invention also encompasses purified TIMP-4.

The invention further provides diagnostic kits for the detection of naturally occurring TIMP-4 and provides for the use of purified TIMP-4 as a positive control and to produce anti-TIMP-4 antibodies. These antibodies may be used to detect conditions which involve abnormal TIMP-4 expression, for example, to diagnose nonhealing corneal or diabetic ulcers or lesions caused by microorganisms.

The invention further provides for methods of treatment of conditions associated with excessive expression of MMPs, such as metastasis of neoplastic cells, angiogenesis and growth of tumors such as cervical, uterine, pancreatic, colon or intestinal carcinomas, osteoarthritis, osteoporosis, pulmonary emphysema, periodontal disease, and rheumatoid arthritis. In addition, the invention provides for the use of TIMP-4 as a means of birth control, ie, to neutralize MMP activity, thereby preventing implantation of the embryo. Each of these uses would include administration of effective amounts of purified TIMP-4 or vectors comprising nucleic acid sequences encoding TIMP-4 to individuals subject to these conditions for the purpose of inhibiting MMP expression.

The invention also provides pharmaceutical compositions comprising vectors containing the nucleic acid sequence encoding TIMP-4 or purified TIMP-4 protein which can be used in the prevention or treatment of various conditions including, but not limited to, metastasis of neoplastic cells, angiogenesis and growth of tumors such as cervical, uterine, pancreatic, colon or intestinal carcinomas, pregnancy, osteoarthritis, osteoporosis, pulmonary emphysema, periodontal disease, and rheumatoid arthritis. For example, TIMP-4 may be used in inhibiting or neutralizing metalloproteinase activity associated with excessive expression of gelatinases in the alveolar structure of the lung which leads to pulmonary emphysema. Oligonucleotides or fragments of the nucleotide sequence and antagonists and inhibitors of the protein may be administered to neutralize the activity of TIMP-4 in situations where TIMPs are overexpressed, for example, during the healing of conditions such as corneal and diabetic ulcers, and ulcers/lesions caused by microorganisms.

DESCRIPTION OF THE FIGURES

FIG. 1 displays the nucleic acid, SEQ. ID. NO.:1, and amino acid sequences of TIMP-4 from human uterus. Sequences shown in this and the following figure were produced using the multisequence alignment program of DNASTAR software (DNASTAR Inc, Madison, Wis.).

FIG. 2 shows the amino acid sequence alignment between TIMP-4, SEQ. ID. NO.:2, and TIMP-2, SEQ. ID. NO.:3. The alignments for this and FIG. 3 were produced using INHERIT™ Sequence Analysis (Applied Biosystems Inc, Foster City, Calif.).

FIG. 3 shows the amino acid sequence alignment between TIMP-4, SEQ. ID. NO.:2, and TIMP-3, SEQ. ID. NO.:4.

FIG. 4 shows the amino acid sequence alignment between TIMP-4, SEQ. ID. NO.:2, and TIMP-1, SEQ. ID. NO.:5, using the Clustal program of DNASTAR software.

DETAILED DESCRIPTION OF THE INVENTION

The present invention relates to a novel tissue inhibitor of metalloproteinases, TIMP-4, whose nucleic acid sequence was identified among the polynucleotides of a uterine tissue library (UTRSNOT01) and to the use of the nucleic acid and amino acid sequences of TIMP-4 in the study, diagnosis, prevention and treatment of disease.

The polynucleotide sequence encoding TIMP-4 was first identified within Incyte Clone No. 589345. A BLAST search (Basic Local Alignment Search Tool; Altschul S. F. (1993) J Mol Evol 36:290–300; Altschul, S. F. et al (1990) J Mol Biol 215:403–10) comparing the cDNAs of the UTRSNOT01 library against the primate database of GenBank 91 identified Incyte Clone 589345 as a nonexact homolog of human metalloproteinase inhibitor. Incyte Clone 589345 was resequenced and the deduced amino acid sequence compared with a consensus sequence for the known TIMP molecules. The relationships of the TIMP molecules, one to another, can be described on the basis of their comparison to the amino acid consensus sequence: TIMP-2 shows 62% homology to the amino acid consensus sequence; TIMP-4, 61% homology; TIMP-3, 56% homology; and TIMP-1, 43% homology. Therefore, in series, TIMP-4 is most closely related to TIMP-2, closely related to TIMP-3 and related to TIMP-1. The exact relationships of each of the known TIMPs to TIMP-4 are shown in FIGS. 2 through 4.

The present invention is based, in part, on the amount of amino acid sequence and structural homology among the TIMP molecules, and on the fact that all of the known TIMPs have been found in female reproductive tissues. The protein TIMP-4 has a length of 224 amino acids with a 5' signal sequence of 29 residues, $M_1$ through $A_{29}$, and displays 30% amino acid sequence identity with the deduced sequence of human TIMP-2. Other significant features of TIMP-4 include the presence of the VIRAK motif, at amino acid residues 47–51 of SEQ ID NO:2, which indicates that TIMP-4 interacts with $Zn^-$(Williamson R. A. et al. (1994) Protein Eng 7:1035–1040) and the presence of the 12 cysteine residues common to the known TIMPs (FIGS. 2–4; Negro A. et al. (1995) FEBS Letc 360:52–56). TIMP-4 lacks the 3' NAT glycosylation site which is located five amino acid residues before the stop codon of TIMP-3 (FIG. 3), but the mature protein which begins at $C_{30}$ of SEQ ID NO:2 has five asparagines, at least five of which may associate with carbohydrate moieties.

The use of TIMP-4, and of the nucleic acid sequences which encode it, is based on the amino acid and structural homologies between TIMP-4 and the other known TIMPs and on the ability of the known TIMPS to inhibit the activities of MMPs. The timing of and amount of expression of MMPs and TIMPs are implicated in metastasis of neoplastic cells, angiogenesis and growth of tumors such as cervical, uterine, pancreatic, colon or intestinal carcinomas, osteoarthritis, osteoporosis, pulmonary emphysema, periodontal disease, rheumatoid arthritis, corneal or diabetic ulcers or lesions caused by microorganisms. In each of the next three situations, the level of MMP expression precedes or exceeds the expression of TIMP.

MMPs play a role in loosening the components of the extracellular matrix of veins and arteries and easing the passage of various cell types. In the same manner, neoplastic cells enter and exit the vascular system of individuals with metastatic carcinomas (Ray J. M. and Stetler-Stevenson W. G., (supra) and Mignatti P. and Rifkin D. B. (supra). Supplying purified TIMP-4 to those individuals would inhibit MMPs and interfere with metastasis of neoplastic cells. Similarly, supplying purified TIMP-4 to individuals with developing tumors would interfere with MMP-associated angiogenesis, the vascularization of the tumor and inhibit tumor growth.

In reproductive studies, Reponen P. et al. (supra) has shown that the trophoblast secretes MMPs during implantation of the embryo. The timely inhibition of these MMPs, post coitus, by supplying women with recombinant TIMP-4 would inhibit the MMPs and prevent loosening of the extracellular matrix, implantation and pregnancy.

In diseases such as osteoarthritis, rheumatoid arthritis, pulmonary emphysema, periodontal disease, and osteoporosis, the excess MMPs cause inflammation, tissue destruction and impaired function. Delivery of TIMP-4 to the tissue or disease site would inhibit the activity of the MMPs and reduce inflammation and damage.

Alternatively, induction and overexpression of TIMPs by insult or injury, and in the presence of a systemic disease such as diabetes, results in recalcitrant wound healing (Wentworth J. S. et al, supra; Burns F. R. et al, supra). Inhibiting or downregulating TIMP expression through the delivery of antisense molecules, antibodies, antagonists or inhibitors to the subject's ulcer or lesion would allow the MMPs to carry out normal tissue remodeling processes.

"Nucleic acid sequence" as used herein refers to an oligonucleotide, nucleotide or polynucleotide sequence, and fragments or portions thereof, and to DNA or RNA of genomic or synthetic origin which may be single-stranded or double-stranded, and represent the sense or antisense strand. Similarly, amino acid sequence as used refers to an oligopeptide, peptide, polypeptide or protein sequence.

As used herein, "TIMP-4" refers to TIMP-4 protein from any species, including, bovine, ovine, porcine, equine, murine and preferably human, in a naturally occurring form or from any source, whether natural, synthetic, semi-synthetic or recombinant. As used herein, "naturally occurring" refers to a molecule, nucleic acid or amino acid sequence, found in nature.

The present invention also encompasses TIMP-4 variants. A preferred TIMP-4 variant is one having at least 80% amino acid sequence similarity, a more preferred TIMP-4 variant is one having at least 90% amino acid sequence similarity and a most preferred TIMP-4 variant is one having at least 95% amino acid sequence similarity to the TIMP-4 amino acid sequence (SEQ ID NO:2). A "variant" of TIMP-4 may have an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

Similarly, the term "biologically active" refers to a TIMP-4 having structural, regulatory or biochemical functions of the naturally occurring TIMP-4. Likewise, "immunological activity" is defined as the capability of the natural, recombinant or synthetic TIMP-4, or any oligopeptide thereof, to induce a specific immune response in appropriate animals or cells and to bind with specific antibodies.

The term "derivative" refers to the chemical modification of the encoded TIMP-4. Illustrative of such modifications would be replacement of hydrogen by an alkyl, acyl, or amino group. A TIMP-4 derivative would encode a polypeptide which retains essential biological characteristics of TIMPs such as, for example, the inhibition of MMPs.

As used herein, the term "purified" refers to molecules, either nucleic or amino acid sequences, that are removed from their natural environment and isolated or separated from at least one other component with which they are naturally associated.

The TIMP-4 Coding Sequences

Figure 1A:
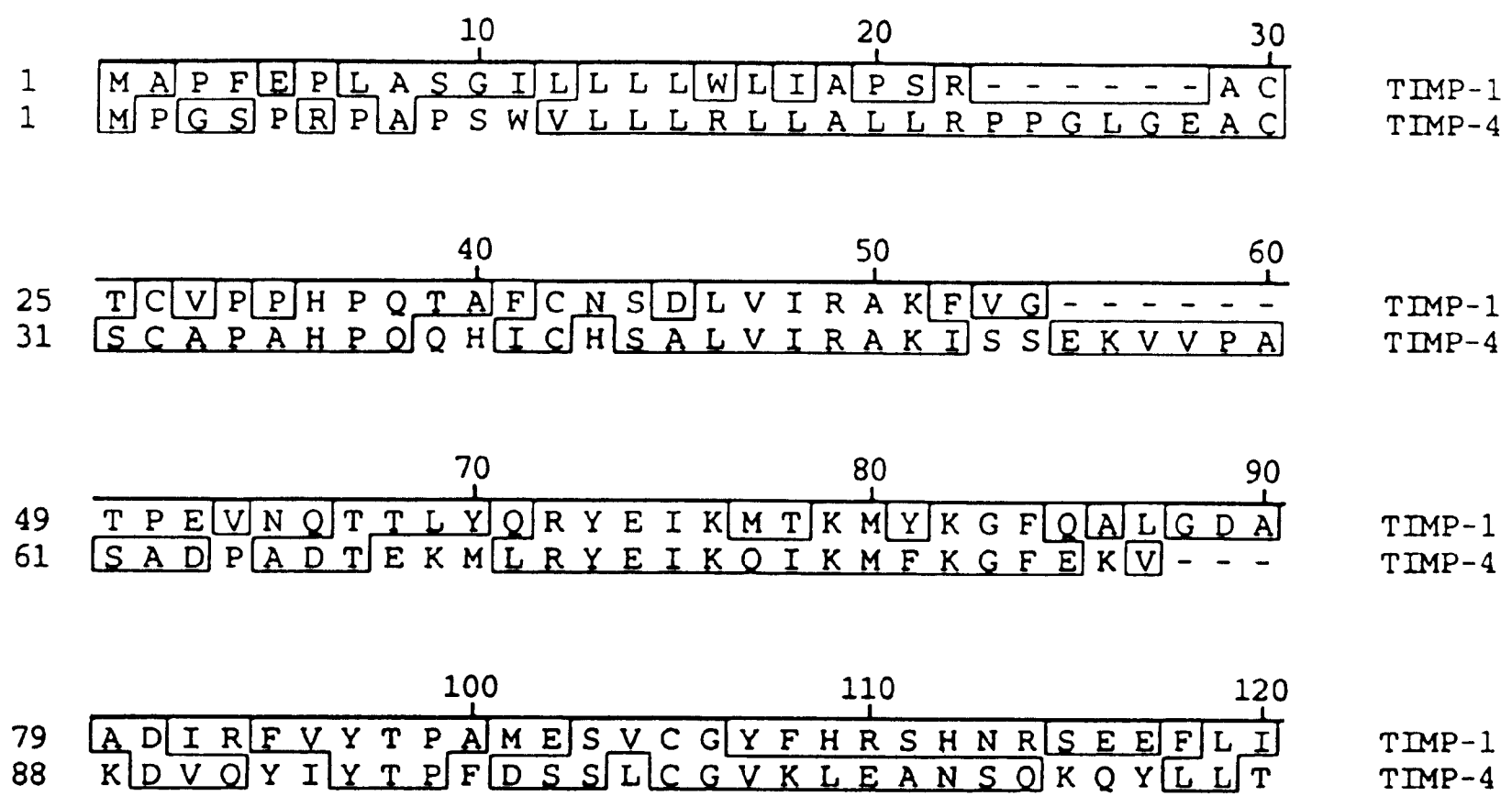

The determined nucleic acid and deduced amino acid sequences of TIMP-4 are shown in FIG. 1. In accordance with the invention, any nucleotide sequence which encodes the amino acid sequence of TIMP-4 can be used to generate recombinant molecules which express TIMP-4. In a specific embodiment described herein, TIMP-4 was first isolated and identified within Incyte Clone 589345 from human uterus (UTRSNOT01) library.

Methods for DNA sequencing are well known in the art and employ such enzymes as the Klenow fragment of DNA polymerase I, Sequenase® (US Biochemical Corp, Cleveland, Ohio), Taq polymerase (Perkin Elmer, Foster City, Calif.), thermostable T7 polymerase (Amersham, Chicago, Ill.), or combinations of recombinant polymerases and proofreading exonucleases such as the ELONGASE Amplification System marketed by Gibco BRL (Gaithersburg Md.). Methods to extend the DNA from an oligonucleotide primer annealed to the DNA template of interest have teen developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno, Nev.), Peltier Thermal Cycler (PTC200; MJ Research, Watertown, Mass.) and the Applied Biosystems (Foster City, Calif.) Catalyst 800 and 377 and 373 DNA sequencers.

The quality of any particular cDNA library may be determined by performing a pilot scale analysis of the cDNAs and checking for percentages of clones containing vector, lambda or E. coli DNA, mitochondrial or repetitive DNA, and clones with exact or homologous matches to public databases.

Extending TIMP-4 Polynucleotide Sequence

The polynucleotide sequence of TIMP-4 may be extended utilizing partial nucleotide sequence and various methods known in the art to detect upstream sequences such as promoters and regulatory elements. Gobinda et al (1993; PCR Methods Applic 2:318–22) disclose "restriction-site polymerase chain reaction (PCR)" as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T. et al (1988) Nucleic Acids Res 16:8186). The primers may be designed using Oligo 4.0 (National Biosciences Inc, Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M. et al (1991) PCR Methods Applic 1:111–19) is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR.

Parker J. D. et al (1991; Nucleic Acids Res 19:3055–60), teach walking PCR, a method for targeted gene walking which permits retrieval of unknown sequence. PromoterFinder™ a new kit available from Clontech (Palo Alto, Calif.) uses PCR, nested primers and special libraries to "walk in" genomic DNA. This process avoids the need to screen libraries and is useful in finding intron/exon junctions.

Another PCR method, "Improved Method for Obtaining Full Length cDNA Sequences" by Guegler et al, patent application Ser. No. 08/487,112, filed Jun. 7, 1995 and hereby incorporated by reference, employs XL-PCR™ (Perkin-Elmer, Foster City, Calif.) to amplify and/or extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extending sequence into the gene's promoter binding region.

A new method for either analyzing the size or confirming the nucleotide sequence of sequencing or PCR products is capillary electrophoresis. Systems for rapid sequencing are available from Perkin Elmer, Beckman Instruments (Fullerton, Calif.), and other companies. Capillary sequencing employs flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg, Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851–8).

Expression of TIMP-4 Nucleotide Sequence

In accordance with the present invention, TIMP-4 polynucleotide sequences which encode TIMP-4, as well as fragments, fusion proteins or functional equivalents thereof, may be used to generate recombinant DNA molecules that direct the expression of TIMP-4 in appropriate host cells. Due to the inherent degeneracy of the genetic code, other DNA sequences which encode substantially the same or a functionally equivalent amino acid sequence, may be used to clone and express TIMP-4. As will be understood by those of skill in the art, it may be advantageous to produce TIMP-4-encoding nucleotide sequences possessing non-naturally occurring codons. Codons preferred by a particular prokaryotic or eukaryotic host (Murray E. E. (1989) Nuc Acids Res 17:477–508) can be selected, for example, to increase the rate of TIMP-4 expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of SEQ ID NO:1 under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152, Academic Press, San Diego, Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low-stringency" at about 20° C. to 25° C. below Tm. As will be understood by those of skill in the art, a maximum stringency hybridization can be used to identify or detect identical or allelic polynucleotide sequences while an intermediate (or low) stringency hybridization can be used to identify or detect related polynucleotide sequences. The term "hybridization" as used herein shall include "the process by which a strand of nucleic acid joins with a complementary strand through base pairing" (Coombs J. (1994) *Dictionary of Biotechnology*, Stockton Press, New York, N.Y.) as well as the process of amplification which is carried out in polymerase chain reaction technologies as described in Dieffenbach C. W. and G. S. Dveksler (1995, *PCR Primer, a Laboratory Manual*, Cold Spring Harbor Press, Plainview, N.Y.) and incorporated herein by reference.

As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring TIMP-4.

As used herein "substitution" results from the replacement of one or more nucleotides or amino acids by different nucleotides or amino acids, respectively.

Derivative TIMP-4 polynucleotide sequences which may be used in accordance with the invention include deletions, insertions or substitutions of different nucleotide residues resulting in a polynucleotide that encodes the same or a functionally equivalent TIMP-4. The protein may also show deletions, insertions or substitutions of amino acid residues which produce a silent change and result in a functionally equivalent TIMP-4. Variant molecules may be synthesized by deliberate amino acid substitution. Such variants are based on the similarity in polarity, charge, solubility, hydrophobicity, hydrophilicity, and/or the amphipathic nature of the residues as long as the biological activity of TIMP-4 is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine, asparagine, glutamine; serine, threonine, phenylalanine, and tyrosine.

Included within the scope of the present invention are alleles of TIMP-4. As used herein, an "allele" or "allelic sequence" is an alternative form of TIMP-4. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention may be engineered in order to alter a TIMP-4 coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, etc.

In another embodiment of the invention, a natural, modified or recombinant TIMP-4 sequence may be ligated to a heterologous sequence to encode a fusion protein. For example, for screening of peptide libraries for inhibitors of TIMP-4 activity, it may be useful to encode a chimeric TIMP-4 protein expressing a heterologous epitope that is recognized by a commercially available antibody. A fusion protein may also be engineered to contain a cleavage site located between a TIMP-4 sequence and the heterologous protein sequence, so that the TIMP-4 may be cleaved and purified away from the heterologous moiety.

In an alternate embodiment of the invention, the entire coding sequence of TIMP-4, or any part thereof, could be synthesized using chemical methods (Sindelar L. E. and J. M. Jaklevic (1995) Nuc Acids Res 23:982–7; Modesti A. et al (1993) Biochim Biophys Acta 1216:369–74). Similarly, the protein itself could be produced using chemical methods. For example, peptides can be synthesized by solid phase techniques, cleaved from the resin, and purified by preparative high performance liquid chromatography (eg, Creighton (1983) *Proteins Structures and Molecular Principles*, W. H. Freeman and Co, New York, N.Y.). The composition of the synthetic peptides may be confirmed by amino acid analysis or sequencing (eg, using the Edman degradation procedure and deduced translation from the nucleotide sequence as reported in Castalano-Sherman J. et al (1993) J Dental Res 72:1566–72).

Direct peptide synthesis can be performed using various solid-phase techniques (Roberge J. Y. et al (1995) Science 269:202–204) and automated synthesis may be achieved, for example, using Applied Biosystems 431A Peptide Synthesizer in accordance with the instructions provided by the manufacturer. Additionally the amino acid sequence of TIMP-4, or any part thereof, may be altered during direct synthesis and/or combined using chemical methods with other TIMP sequences, or any part thereof, to produce a variant polypeptide.

Expression Systems for TIMP-4 Nucleotide Sequences

In order to express a biologically active TIMP-4, the nucleotide sequence coding for TIMP-4, or a functional equivalent, is inserted into an appropriate expression vector, ie, a vector which contains the necessary elements for the transcription and translation of the inserted coding sequence.

Methods which are well known to those skilled in the art can be used to construct expression vectors containing a TIMP-4 coding sequence and appropriate transcriptional or translational controls. These methods include in vitro recombinant DNA techniques, synthetic techniques and in vivo recombination or genetic recombination. Such techniques are described in Maniatis et al. (1989) *Molecular Cloning, A Laboratory Manual*, Cold Spring Harbor Press, Plainview, N.Y. and Ausubel F. M. et al. (1989) *Current Protocols in Molecular Biology*, John Wiley & Sons, New York, N.Y.

A variety of expression vector/host systems may be utilized to express a TIMP-4 coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters such as those discussed in Baeuerle, Pa. (1995) *Inducible Gene Expression*, Vol 1 and 2, Birkhauser, Cambridge, Mass. For example, when cloning in bacterial systems, inducible promoters such as the hybrid lacZ promoter of the Bluescript® phagemid (Stratagene, LaJolla, Calif.) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of the TIMP-4 nucleotide sequence, vectors based on SV40 or EBV may be used with an appropriate selectable marker.

In bacterial systems, a number of expression vectors may be selected depending upon the use intended for TIMP-4. For example, when large quantities of TIMP-4 are needed for the induction of antibodies, vectors which direct high level expression of fusion proteins that are readily purified may be desirable. Such vectors include, but are not limited to, the *E. coli* cloning and expression vector Bluescript® (Stratagene), in which the TIMP-4 coding region may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a TIMP-4 coding sequence may be driven by any of a number of promoters. For example, viral promoters such as the 35S and 19S promoters of CaMV (Brisson et al (1984) Nature 310:511–514) may be used alone or in combination with the cDNA version of the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843): or heat shock promoters (Winter J. and Sinibaldi R. M. (1991) Results Probl Cell Differ 17:85–105) may be used. These constructs can be introduced into plant cells by direct DNA transformation or pathogen-mediated transfection. For reviews of such techniques, see Hobbs S. or Murry L. E. in McGraw Yearbook of Science and Technology (1992) McGraw Hill New York, N.Y., pp 191–196 or Weissbach and Weissbach (1988) Methods for Plant Molecular Biology, Academic Press, New York, N.Y., pp 421–463.

An alternative expression system which could be used to express TIMP-4 is an insect system. In one such system, *Autographa californica* nuclear polyhedrosis virus (AcNPV) is used as a vector to express foreign genes in *Spodoptera frugiperda* cells or in Trichoolusia larvae. The TIMP-4 coding sequence may be cloned into a non-essential region of the virus, such as the polyhedrin gene, and placed under control of the polyhedrin promoter. Successful insertion of TIMP-4 will render the polyhedrin gene inactive and produce recombinant virus lacking coat protein. The recombinant viruses are then used to infect *S. frugiperda* cells or Trichoplusia larvae in which TIMP-4 is expressed (Smith et al (1983) J Virol 46:584; Engelhard E. K. et al (1994) Proc Nat Acad Sci 91:3224–7).

In mammalian host cells, a number of viral-based expression systems may be utilized. In cases where an adenovirus is used as an expression vector, a TIMP-4 coding sequence may be ligated into an adenovirus transcription/translation complex consisting of the late promoter and tripartite leader sequence. Insertion in a non-essential E1 or E3 region of the viral genome will result in a viable virus capable of expressing TIMP-4 in infected host cells. (Logan and Shenk (1984) Proc Natl Acad Sci 81:3655–3659). In addition, transcription enhancers, such as the rous sarcoma virus (RSV) enhancer, may be used to increase expression in mammalian host cells.

Specific initiation signals may also be required for efficient translation of an inserted TIMP-4 coding sequences. These signals include the ATG initiation codon and adjacent sequences. In cases where TIMP-4, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express TIMP-4 may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection and its presence allows growth and recovery of cells which are successfully expressing the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler et al (1977) Cell 11:223) and adenine phosphoribosyltransferase (Lowy et al (1980) Cell 22:817) genes which can be employed in tk$^-$ or aprt$^-$cells, respectively. Also, antimetabolite, antibiotic or herbicide resistance can be used as the basis for selection; for example, dhfr which confers resistance to methotrexate (Wigler et al (1980) Natl Acad Sci 77:3567); npt, which confers resistance to the aminoglycosides neomycin and G-418 (Colberre-Garapin et al (1981) J Mol Biol 150:1) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman and Mulligan (1988) Proc Natl Acad Sci 85:8047). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C. A. et al (1995) Methods Mol Biol 55:121–31).

Identification of Transformants Containing Nucleotides Encoding TIMP-4

Although the presence/absence of marker gene expression suggests that the gene of interest is also present, its presence and expression should be confirmed. For example, if the TIMP-4 is inserted within a marker gene sequence, recombinant cells containing TIMP-4 can be identified by the absence of marker gene function. Alternatively, a marker gene can be placed in tandem with a TIMP-4 sequence under the control of a single promoter. Expression of the marker gene in response to induction or selection will usually result in expression of TIMP-4 as well.

Alternatively, host cells which contain the coding sequence for TIMP-4 and express TIMP-4 may be identified by a variety of procedures known to those of skill in the art. These procedures include, but are not limited to, DNA-DNA or DNA-RNA hybridization and protein bioassay or immunoassay techniques which include membrane, solution, or chip-based technologies for the detection and/or quantification of the nucleic acid or protein.

The presence of the TIMP-4 polynucleotide sequence can be detected by DNA-DNA or DNA-RNA hybridization or amplification using probes, portions or fragments of TIMP-4. Nucleic acid amplification based assays involve the use of oligonucleotides or oligomers based on the TIMP-4 sequence to detect transformants containing TIMP-4 DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

Sequences for the Expression and Recovery of TIMP-4 Protein

Host cells transformed with a TIMP-4 nucleotide sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing TIMP-4 can be designed with signal sequences which direct secretion of TIMP-4 through a particular prokaryotic or eukaryotic cell membrane. Other recombinant constructions may join TIMP-4 to nucleotide sequence encoding a polypeptide domain which will facilitate purification of soluble proteins (Kroll D. J. et al (1993) DNA Cell Biol 12:441–53; see also above discussion of vectors containing fusion proteins).

TIMP-4 may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequences such as Factor XA or enterokinase (Invitrogen, San Diego, Calif.) between the purification domain and TIMP-4 is useful to facilitate purification.

Detection of the Expressed and Activity of TIMP-4 Protein

A variety of protocols for detecting and measuring the expression of TIMP-4, using either polyclonal or monoclonal antibodies specific for TIMP-4 are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on TIMP-4 is preferred, but a competitive binding assay may be employed. These and other assays are described, among other places, in Hampton R. et al (1990, *Serological Methods, a Laboratory Manual*, APS Press, St Paul, Minn.) and Maddox D. E. et al (1983, J Exp Med 158:1211).

The activity of TIMP-4 can be assessed chemically by using expressed TIMP-4 to inhibit the ability of proteolytic enzymes to degrade matrix materials. For example, a simple reverse zymogram, patterned after the technique of Tyagi S. C. et al (1993; Mol Cell Biochem 126:49–59), hereby incorporated by reference, would involve the electrophoresis of different concentrations of TIMP-4 or media containing TIMP-4. The resulting gel or an electroblot of that gel would be coated or soaked in gelatin. Then, gelatinase would be used to digest away the gelatin. In those areas of the gel or blot where the gelatin was in contact with TIMP-4, digestion would be inhibited. The inhibition associated with different concentrations of TIMP-4 could be used to quantitatively to assess TIMP-4 activity. Similar gels could be run using collagen/collagenase or other extracellular matrix components and their enzymes.

Labeling Nucleotides or Antibodies for TIMP-4 Assays

A wide variety of labels and conjugation techniques are known by those skilled in the art and can be used in various nucleic and amino acid assays. Means for producing labeled hybridization or PCR probes for detecting sequences related to TIMP-4 include oligolabeling, nick translation, end-labeling or PCR amplification using a labeled nucleotide. Alternatively, the TIMP-4 sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Uses of TIMP-4

The rationale for using TIMP-4 diagnostically and therapeutically is based on its amino acid sequence, its structural similarity to other TIMPs, and the known activities of TIMP molecules. All of the known TIMPs degrade MMPs, therefore TIMP-4 can be used in conditions associated with a surplus of MMPs, ie, any condition where the amount of MMPs is excessive and amount of TIMP is insufficient to inhibit that quantity of MMPs. Such conditions are exemplified by metastasis of neoplastic cells, angiogenesis and growth of cervical, uterine, pancreatic, colon or intestinal carcinomas, osteoarthritis, osteoporosis, pulmonary emphysema, periodontal disease, and rheumatoid arthritis.

TIMP-4 can also be used to prevent metastasis of neoplastic cells and vascularization of tumors. Tumor-produced MMPs loosen the extracellular matrix of the tumor allowing neoplastic cells to escape from the original tumor site. Then, the neoplastic cells produce MMPs which dissolve a path through surrounding tissues and breach the basement membranes and endothelial walls of the vascular system. Inhibition of the MMPs by TIMP-4 can prevent the metastasis of neoplastic cells. Similarly, tumor-produced MMPs loosen the extracellular matrix of developing tumors allowing the tissue mass to grow and permitting angiogenesis. Inhibition of the MMPs by TIMP-4 can prevent tumor growth and angiogenesis.

TIMP-4 can also be used for post-coital birth control. The trophoblast secretes MMPs during implantation of the embryo. The timely inhibition of these MMPs by recombinant TIMP-4, post coitus, would prevent loosening of the extracellular matrix, implantation of the embryo, and therefore, pregnancy.

Because some conditions associated with high MMP/TIMP ratio, such as osteoarthritis, result in inflammation and pain, TIMP-4 also can have a role in controlling inflammation and inflammation-associated pain. For example, a therapeutic molecule comprising TIMP-4 or vectors encoding TIMP-4 can find application in a disease state such as osteoarthritis where the excessive expression of MMPs causes erosion of connective tissues and can lead to osteoporosis.

In another embodiment of the invention, antisense molecules, anti-TIMP-4 antibodies, antagonists or inhibitors capable of neutralizing the activity of TIMP-4 can be used as therapeutics for conditions characterized by excess expression of TIMP-4. High TIMP-4 expression may interfere with the healing process by preventing MMPs from tearing down matrix materials, such as in corneal or diabetic ulcers or ulcers/lesions caused by microorganisms, such as Helicobacter, Hemophilus, Treponema, or Neisseria. In such cases, the exposure to invading microorganisms, mitogens or toxic materials induces expression of TIMP-4 early in the disease process. Inhibition of the MMPs by TIMP-4 slows removal of dead or damaged cells which is necessary to create an environment for healing. Excessive TIMP-4 prevents the removal of injured matrix and interferes with tissue remodeling and healing.

TIMP-4 Antibodies

Procedures well known in the art can be used for the production of antibodies to TIMP-4. Such antibodies include, but are not limited to, polyclonal, monoclonal, chimeric, single chain, Fab fragments and fragments produced by a Fab expression library. Neutralizing antibodies, ie, those which inhibit biological activity of TIMP-4, are especially preferred for diagnostics and therapeutics.

For the production of antibodies, various hosts including goats, rabbits, rats, mice, etc. may be immunized by injection with TIMP-4 or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to TIMP-4 may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R. Liss Inc, New York, N.Y., pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce TIMP-4-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G. and Milstein C. (1991; Nature 349:293–299).

Antibody fragments which contain specific binding sites for TIMP-4 may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W. D. et al (1989) Science 256:1275–1281).

TIMP-4-specific antibodies are useful for the diagnosis of conditions and diseases associated with aberrant expression of TIMP-4. A variety of protocols for competitive binding or immunoradiometric assays using either polyclonal or monoclonal antibodies with established specificities are well known in the art. Such immunoassays typically involve the formation of complexes between TIMP-4 and its specific antibody (or TIMP-4-binding molecule) and the measurement of complex formation. A two-site, monoclonal-based immunoassay utilizing monoclonal antibodies reactive to two noninterfering epitopes on a specific TIMP-4 protein is preferred, but a competitive binding assay may also be employed. These assays are described in Maddox D. E. et al (1983, J Exp Med 158:1211).

Diagnostic Assays Using TIMP-4 Specific Antibodies

Particular TIMP-4 antibodies are useful for the diagnosis of conditions or diseases characterized by aberrant expression of TIMP-4. Diagnostic assays for TIMP-4 include methods utilizing the antibody and a label to detect TIMP-4 in human body fluids, cells, tissues or extracts of such tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring TIMP-4, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on TIMP-4 is preferred, but a competitive binding assay may be employed. These assays are described, among other places, in Maddox, D. E. et al (1983, J Exp Med 158:1211).

In order to provide a basis for the diagnosis of disease, normal or standard values for TIMP-4 expression must be established. This is accomplished by combining body fluids or cell extracts taken from normal subjects, either animal or human, with antibody to TIMP-4 under conditions suitable for complex formation which are well known in the art. The amount of standard complex formation may be quantified by comparing it with a dilution series of positive controls where a known amount of antibody is combined with known concentrations of purified TIMP-4. Then, standard values obtained from normal samples may be compared with values obtained from samples from subjects potentially affected by a disorder or disease related to TIMP-4 expression. Deviation between standard and subject values establishes the presence of disease state.

Drug Screening

TIMP-4, its catalytic or immunogenic fragments or oligopeptides can be used for screening therapeutic compounds in any of a variety of drug screening techniques. The fragment employed in such a test may be free in solution, affixed to a solid support, borne on a cell surface, or located intracellularly. The abolition of catalytic activity or the formation of binding complexes, between TIMP-4 and the agent being tested, may be measured.

Another technique for drug screening which provides for high throughput screening of compounds having suitable binding affinity to the TIMP-4 is described in detail in "Determination of Amino Acid Sequence Antigenicity" by Geysen H. N., WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of TIMP-4 and washed. Bound TIMP-4 is then detected by methods well known in the art. Purified TIMP-4 can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding TIMP-4 specifically compete with a test compound for binding TIMP-4. In this manner, the antibodies can be used to detect the presence of any peptide which shares one or more antigenic determinants with TIMP-4.

Uses of TIMP-4 Polynucleotide

A TIMP-4 polynucleotide, or any part thereof, may be used for diagnostic and/or therapeutic purposes. For diagnostic purposes, the TIMP-4 of this invention may be used to detect and quantitate gene expression in conditions or diseases in which TIMP-4 activity may be implicated. These specifically include, but are not limited to, metastasis of neoplastic cells, angiogenesis and growth of tumors, cervical, uterine, pancreatic, colon or intestinal carcinomas, pregnancy, osteoarthritis, osteoporosis, pulmonary emphysema, periodontal disease, rheumatoid arthritis, corneal and diabetic ulcers, or ulcers/lesions caused by microorganisms. Included in the scope of the invention are oligonucleotide sequences, antisense RNA and DNA molecules and ribozymes, which function to inhibit translation of a TIMP-4.

Another aspect of the subject invention is to provide for hybridization or PCR probes which are capable of detecting polynucleotide sequences, including genomic sequences, encoding TIMP-4 or closely related molecules. The specificity of the probe, whether it is made from a highly conserved region, eg, 10 unique nucleotides in the 5' regulatory region, or a less conserved region, eg, between cysteine residues especially in the 3' region, and the stringency of the hybridization or amplification (high, intermediate or low) will determine whether the probe identifies only naturally occurring TIMP-4 or related sequences.

Diagnostics

TIMP-4 polynucleotide sequences may be used for the diagnosis of conditions or diseases resulting from aberrant expression of TIMP-4. For example, polynucleotide sequences encoding TIMP-4 may be used in hybridization or PCR assays of tissues from biopsies or autopsies to detect abnormalities in TIMP-4 expression. The form of such qualitative or quantitative methods may include Southern or northern analysis, dot blot or other membrane-based technologies; PCR technologies; dip stick, pin, chip and ELISA technologies. All of these techniques are well known in the art, and are in fact the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for TIMP-4 expression must be established. This is accomplished by combining body fluids or cell extracts taken from normal subjects, either animal or human, with TIMP-4 or a portion thereof, under conditions suitable for hybridization or amplification. Standard hybridization may be quantified by comparing the values obtained for normal subjects with a dilution series of positive controls run in the same experiment where a known amount of purified TIMP-4 is used. Standard values obtained from normal samples may be compared with values obtained from samples from subjects potentially affected by a disorder or disease related to TIMP-4 expression. Deviation between standard and subject values establishes the presence of the disease state.

If disease is established, an existing therapeutic agent is administered, and a treatment profile may be generated. Finally, the assay may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195; 4,800,195; and 4,965,188 provides additional uses for oligonucleotides based upon the TIMP-4 sequence. Such oligomers are generally chemically synthesized, but they may be generated enzymatically or produced from a recombinant source. Oligomers generally comprise two nucleotide sequences, one with sense orientation (5'->3') and one with antisense (3'<-5') employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally methods to quantitate the expression of a particular molecule include radiolabeling (Melby P. C. et al 1993 J Immunol Methods 159:235–44) or biotinylating (Duplaa C. et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer-of-interest is presented in various dilutions and a spectrophotometric or calorimetric response gives rapid quantitation. For example, upregulation of TIMP-4 in lung may indicate that the expression of MMPs needs to be monitored since the unopposed activity of MMPs can result in the destruction that is associated with pulmonary emphysema. A definitive diagnosis may allow health professionals to treat the patient and prevent further worsening of the condition. Similarly, assays known to those of skill in the art. can be used to monitor the progress of a patient displaying a TIMP-4 associated disease state during therapy.

Therapeutics

A TIMP-4 sequence may be useful in the treatment of various conditions or diseases. By introducing TIMP-4 sequence into cells, gene therapy can be used to treat conditions characterized by underexpression of TIMP-4. In some instances, the sequence encoding a TIMP-4 is intended to replace or act in the place of a functionally deficient naturally occurring gene.

Expression vectors derived retroviruses, adenovirus, herpes or vaccinia viruses, or from various bacterial plasmids, may be used for delivery of recombinant TIMP-4, sense or antisense molecules, to the targeted cell population. Methods which are well known to those skilled in the art can be used to construct recombinant vectors containing TIMP-4. See, for example, the techniques described in Maniatis et al (supra) and Ausubel et al(supra). Alternatively, recombinant TIMP-4 can be delivered to target cells in liposomes.

Conditions or diseases characterized by excess TIMP-4 can be treated by using the same gene therapy techniques to introduce recombinant antisense constructs. The successful delivery and expression of such sequences will modulate or inhibit the transcription of TIMP-4 mRNA.

The full length cDNA sequence and/or its regulatory elements enable researchers to use TIMP-4 as a tool in sense (Youssoufian H. and H. F. Lodish 1993 Mol Cell Biol 13:98–104) or antisense (Eguchi et al (1991) Annu Rev Biochem 60:631–652) investigations or regulation of gene function. Oligonucleotides, designed from the cDNA or control sequences obtained from the genomic DNA can be used in vitro or in vivo to inhibit expression. Such technology is now well known in the art, and sense or antisense oligomers, or larger fragments, can be designed from various locations along the coding or control regions.

TIMP-4 can be turned off by transfecting a cell or tissue with expression vectors which express high levels of a TIMP-4 fragment. Such constructs can flood cells with untranslatable sense or antisense sequences. Even in the absence of integration into the DNA, such vectors may continue to transcribe RNA molecules until all copies are disabled by endogenous nucleases. Such transient expression may last for a month or more with a non-replicating vector (Mettler I., personal communication) and even longer if appropriate replication elements are part of the vector system.

On the other hand, stable transformation of appropriate germ line cells, or preferably a zygote, with a vector containing the TIMP-4 fragments may produce a transgenic organism (U.S. Pat. No. 4,736,866, Apr. 12, 1988), which produces enough copies of the sense or antisense sequence to significantly compromise or entirely eliminate activity of the naturally occurring TIMP-4 gene.

As mentioned previously, modifications of gene expression can be obtained by designing antisense sequences to the control regions of the TIMP-4 gene, ie, the promoters, enhancers, and introns. Oligonucleotides derived from the transcription initiation site, eg, between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that can specifically and efficiently catalyze endonucleolytic cleavage of TIMP-4 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridization with complementary oligonucleotides using ribonuclease protection assays.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

Methods for introducing vectors into cells or tissue include those methods discussed infra. In addition, several of these transformation or transfection methods are equally suitable for the ex vivo therapy, the introduction of vectors into stem cells taken from the patient and clonally propagated for autologous transplant as in U.S. Pat. Nos. 5,399,493 and 5,437,994, disclosed herein by reference.

Furthermore, the TIMP-4 polynucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Polynucleotide Sequences Related to TIMP-4

The nucleic acid sequence for TIMP-4 can also be used to generate hybridization probes for mapping the naturally occurring genomic sequence. The sequence may be mapped to a particular chromosome or to a specific region of the chromosome using well known techniques. These include in situ hybridization to chromosomal spreads (Verma et al (1988) *Human Chromosomes: A Manual of Basic Techniques*, Pergamon Press, New York City), flow-sorted chromosomal preparations, or artificial chromosome constructions such as YACs, bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. between normal, carrier or affected individuals.

Pharmaceutical Compositions

The present invention comprises pharmaceutical compositions which may comprise all or portions of TIMP-4 or inhibitors of TIMP-4 including antibodies and antagonists, alone or in combination with at least one other agent, such as stabilizing compound, which may be administered in any sterile, biocompatible pharmaceutical carrier, including, but not limited to, saline, buffered saline, dextrose, and water.

TIMP-4 can be administered to a patient alone, or in combination with other TIMPs, agents, drugs or hormones in pharmaceutical compositions where it is mixed with excipient(s) or pharmaceutically acceptable carriers. In one embodiment of the present invention, the pharmaceutically acceptable carrier is pharmaceutically inert. Since TIMP-4 is a secreted protein which works extracellularly to inhibit secreted MMPs, the preferred route for administration of TIMP-4 or its inhibitors is by diffusion from the site of administration.

TIMP-4 may be used alone or in combination with other TIMP molecules to prevent metastasis of neoplastic cells, growth or vascularization of tumors and with other chemotherapy for treating cervical, uterine, pancreatic, colon or intestinal carcinomas. TIMP-4 is administered intraarterially in a sufficient amount to inhibit tumor-produced metalloproteinases from loosening the tumor tissue for angiogenesis, dissolving a path through surrounding tissues, and breaching the basement membranes and endothelial walls of the vascular system, thereby preventing the metastasis of neoplastic cells.

Administration of compounds to treat osteoarthritis has been local or systemic; however, TIMP-4 could also be injected directly into a swollen joint or delivered in combination with a penetrating agent, by patch applied over the joint. Systemic delivery for osteoarthritis or osteoporosis could be via such means as intranasal spray, patch or subcutaneous injection.

TIMP-4 may be used alone or in combination with other TIMP molecules to treat periodontal disease. Administration of a penetrating treatment in a gel, toothpaste, mouthwash, spray or lozenger form could prevent the destruction of connective tissue which eventually results in the loss of teeth. Similarly, administration of TIMP-4 via inhaler could slow or prevent the destruction of connective tissue that alters the alveoli and results in pulmonary emphysema.

An effective amount of TIMP-4, alone or in combination with other TIMPs, may be administered to females as a means for post-coital birth control. TIMPs may be administered from a foam, vaginal sponge, or suppository over approximately a week's time following suspected conception. TIMPs can inactivate the MMPs secreted by trophoblastic cells to begin implantation, thereby preventing pregnancy. This lavage of TIMPs would work prior to and supplement the usual TIMPS which are produced at the implantation site.

Alternatively, for treatment of conditions or diseases characterized by the excessive expression of TIMP-4, such as corneal or diabetic ulcers and ulcers/lesions produced by infectious microorganisms, administration of antisense molecules, antagonists or inhibitors of TIMP-4 may be delivered to wound sites using irrigation, salve or dermal patches or bandages and appropriate penetrant. These molecules can aid in the healing of corneal or diabetic ulcers and ulcers/lesions attributable to microorganisms, alkali burns or other insults or injuries.

Further details on techniques for formulation and administration may be found in the latest edition of "Remington's Pharmaceutical Sciences" (Mack Publishing Co, Easton, Pa.). Although local delivery is desirable, there are other means, for example, oral; parenteral delivery, including intra-arterial (directly to the tumor), intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art.

The pharmaceutical compositions can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. The determination of an effective dose is well within the capability of those skilled in the art, especially in light of the disclosure provided below.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, eg, by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar. alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For administration of TIMP-4, such labeling would include amount, frequency and method of administration.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays, eg, of neoplastic cells. Then, preferably, dosage can be formulated in animal models affected with the neoplasm to achieve a desirable concentration range and route of administration that inhibits MMPs. Such information can be used to determine useful doses and route of administration in humans.

A therapeutically effective dose refers to that amount of TIMP-4 or its inhibitor which ameliorates symptoms, eg, reduces or prevents metastasis of neoplastic cells or prevents implantation. Toxicity and therapeutic efficacy of such compounds can be determined by standard pharmaceutical procedures in cell cultures or experimental animals, eg, for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds, TIMP variants or fragments,which exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for TIMP-4 than for the inhibitors of TIMP-4. Similarly administration of TIMP-4 to a tumor will necessitate delivery in a manner different from that of a TIMP-4 inhibitor being applied to an external ulcer.

It is contemplated that conditions or diseases associated with an insufficiency or excess of TIMP are treatable with either TIMP-4 or inhibitors of TIMP-4, respectively. Conditions associated with production of excess MMPs include, but are not limited to, metastasis of neoplastic cells; angiogenesis and growth of tumors, particularly cervical, uterine, pancreatic, colon or intestinal carcinomas; pregnancy, osteoarthritis, osteoporosis, pulmonary emphysema, periodontal disease, rheumatoid arthritis; whereas conditions or diseases associated with untimely or excessive TIMP-4 may include, but are not limited to, corneal and diabetic ulcers, and ulcers/lesions caused or perpetuated by the presence of microorganisms such as Helicobacter, Hemophilus, Treponema, or Neisseria. The assays previously discussed may be used to diagnose the conditions or diseases and to monitor treatment.

The examples below are provided to illustrate the subject invention. These examples are provided by way of illustration and are not included for the purpose of limiting the invention.

EXAMPLES

I Uterus cDNA Library Construction

The UTRSNOT01 library was constructed using tissue isolated from the uterus of a 59 year old, Caucasian female (Lot#94-072, Keystone Skin Bank, International Institute for the Advancement of Medicine, Exton, Pa.) who died following myocardial infarction. The frozen tissue was ground in a mortar and pestle and lysed immediately in a buffer containing guanidinium isothiocyanate. The lysate was centrifuged over a 5.7M CsCl cushion using an SW28 rotor in a Beckman L8-70M Ultracentrifuge (Beckman Instruments) for 18 hours at 25,000 rpm at ambient temperature. The RNA was extracted once with acid phenol, pH 4.0, precipitated using 0.3M sodium acetate and 2.5 volumes of ethanol, resuspended in water and DNase treated for 15 min at 37° C. The RNA was isolated using the Qiagen Oligotex kit (QIAGEN Inc, Chatsworth, Calif.).

The poly-A+ RNA was handled according to the recommended protocols in the SuperScript Plasmid System for cDNA Synthesis and Plasmid Cloning (Catalog#18248-013; Gibco/BRL). First strand cDNA synthesis was accomplished using oligo d(T) priming and second strand synthesis was performed using a combination of DNA polymerase I, $E.$ $coli$ ligase and RNase H. The cDNA was blunted with T4 polymerase, and a Sal I linker was added to the blunt ended cDNA. The Sal I adapted, double-stranded cDNAs were the digested with Not I and fractionated on a Sepharose CL4B column (Catalog#275105, Pharmacia). Those cDNAs exceeding 400 bp were ligated into pSport I which was subsequently transformed into DH5a™ competent cells (Catalog#18258-012, Gibco/BRL).

II Isolation and Sequencing of cDNA Clones

Plasmid DNA was purified using the Miniprep Kit (catalog # 77468, Advanced Genetic Technologies Corporation, Gaithersburg, Md.), a 96-well block kit with reagents for 960 purifications. The recommended protocol included with the kit was employed except for the following changes. Each of the 96 wells was filled with only 1 ml of sterile Terrific Broth (Catalog # 22711, LIFE TECHNOLOGIES™) with carbenicillin at 25 mg/L and glycerol at 0.4%. After the wells were inoculated, the bacteria were cultured for 24 hours and lysed with 60 μl of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger F. and A. R. Coulson (1975; J Mol Biol 94:441f), using a Hamilton Micro Lab 2200 (Hamilton, Reno, Nev.) in combination with four Peltier Thermal Cyclers (PTC200 from MJ Research, Watertown, Mass.) and Applied Biosystems 377 or 373 DNA Sequencing Systems (Perkin Elmer), and reading frame was determined.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Extension of TIMP-4 to Recover Regulatory Elements

The nucleic acid sequence of full length TIMP-4 (SEQ. ID. NO.:1) may be used to design oligonucleotide primers for obtaining 5' sequences from genomic libraries. One primer is synthesized to initiate extension in the antisense direction (XLR) and the other is synthesized to extend sequence in the sense direction (XLF). The primers allowed the known TIMP-4 sequence to be extended "outward" generating amplicons containing new, unknown nucleotide sequence for the control region of interest. The initial primers may be designed from the cDNA using Oligo 4.0 (National Biosciences Inc, Plymouth, Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

A human genomic library is used to extend and amplify 5' upstream sequence. If necessary, a second set of primers is designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C, the whole transformation mixture is plated on Luria Bertani (LB)-agar (Sambrook J. et al, supra) containing 2× Carb. The following day, several colonies are randomly picked from each plate and cultured in 150 µl of liquid LB/2× carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ. ID. NO.:1 may be employed to screen cDNAs, mRNAs or genomic DNAs. Although the labeling of oligonucleotides, consisting of about 20 base-pairs, is specifically described, essentially the same procedure may be used with larger cDNA fragments. Oligonucleotides are labeled by combining 50 pmol of each oligomer and 250 mCi of [$\gamma$-$^{32}$P] adenosine triphosphate (Amersham, Chicago, Ill.) and T4 polynucleotide kinase (DuPont NEN®, Boston, Mass.). The labeled oligonucleotides are purified with Sephadex G-25 super fine resin column (Pharmacia). A portion containing $10^7$ counts per minute of each is used in a typical membrane based hybridization analysis of human genomic DNA digested with one of the following endonucleases (Ase I, Bgl II, EcoR I, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VI Antisense Molecules

The TIMP-4 sequence, or any part thereof, provide the basis for the design of antisense molecules which may be used to inhibit in vivo or in vitro expression of naturally occurring TIMP-4. Although use of antisense oligomers, consisting of about 20 base-pairs, is specifically described, essentially the same procedure may be used with larger cDNA fragments. An oligonucleotide based on the coding sequence of TIMP-4 may be used to inhibit expression of naturally occurring TIMP-4. The complementary oligonucleotide can be designed from the conserved 5' sequence and used either to inhibit transcription by preventing promoter binding to the upstream nontranslated sequence or translation of a TIMP-4 transcript by preventing the ribosome from binding to the −10 to +10 region of the leader/signal sequence.

VII Expression of TIMP-4

Expression of the TIMP-4 may be accomplished by subcloning the cDNAs into appropriate vectors and transfecting the vectors into host cells. The vector, pBluescript, is used to express TIMP-4 in *E. coli*, strain XL1-BlueMRF™ (Stratagene). Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length TIMP-4. The signal sequence directs the secretion of TIMP-4 into the bacterial growth media which can be used directly in assays for activity as exemplified in Section VIII.

VIII TIMP-4 Activity

TIMP-4 activity is measured using reverse zymography patterned after the method of Tyagi S. C. et al (1993; Mol Cell Biochem 126:49–59). Reverse zymography involves electrophoresis of different concentrations of TIMP-4 or a media containing secreted TIMP-4. The non-denaturing gel in which TIMP-4 has been size separated from other proteins is soaked in gelatin. Then, a time course of digestion with gelatinase is used to assess the activity and effective concentration of TIMP-4 in inhibiting digestion of the gelatin. The control lane shows complete digestion and would be transparent when stained with Comassie Blue, while those lanes containing TIMP-4 show various degrees of gelatin dissolution and differential staining. Similar gels could be run using collagen/collagenase or other extracellular matrix components and their enzymes.

IX Production of TIMP-4 Specific Antibodies

Although TIMP-4 purified using PAGE electrophoresis (Maniatis, supra) can be used to immunize rabbits using standard protocols, a monoclonal approach is more commonly employed. The amino acid sequence translated from TIMP-4 is analyzed using DNASTAR software (DNASTAR Inc) to determine regions of high immunogenicity and a corresponding oligopeptide is synthesized and used to raise antibodies by means known to those of skill in the art. Analysis to select appropriate epitopes, such as those near the C-terminus or in adjacent hydrophilic regions is described by Ausubel F. M. et al (supra).

Typically, the oligopeptides are 15 residues in length, synthesized using an Applied Biosystems Peptide Synthesizer Model 431A using fmoc-chemistry, and coupled to keyhole limpet hemocyanin (K. L. H., Sigma) by reaction with M-maleimidobenzoyl-N-hydroxysuccinimide ester (MBS; Ausubel F. M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

X Purification of Naturally occurring TIMP-4 Using Specific Antibodies

Naturally occurring or recombinant TIMP-4 can be purified by immunoaffinity chromatography using antibodies specific for TIMP-4. An immunoaffinity column is constructed by covalently coupling TIMP-4 antibody to an activated chromatographic resin such as CnBr-activated Sepharose (Pharmacia Biotech). After the coupling, the resin is blocked and washed according to the manufacturer's instructions.

Media containing TIMP-4 is passed over the immunoaffinity column, and the column is washed under conditions that allow the preferential absorbance of TIMP-4 (eg, high ionic strength buffers in the presence of detergent). The column is eluted under conditions that disrupt antibody/TIMP-4 binding (eg, a buffer of pH 2–3 or a high concentration of a chaotrope such as urea or thiocyanate ion), and TIMP-4 is collected.

XI Identification of Molecules Which Interact with TIMP-4

TIMP-4, or biologically active fragments thereof, is labeled with $^{125}$I Bolton-Hunter reagent (Bolton, A. E. and Hunter, W. M. (1973) Biochem J 133: 529). Candidate inhibitory molecules previously arrayed in the wells of a 96 well plate are incubated with the labeled TIMP-4, washed and any wells with labeled TIMP-4 complex are assayed. Data obtained using different concentrations of TIMP-4 are used to calculate values for the number, affinity, and association of TIMP-4 with the candidate inhibitory molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

We claim:

1. An antibody specific for a purified polypeptide comprising amino acid residues 30 through 195 of SEQ. ID. NO.:2.

* * * * *

Adverse Decision In Interference

Patent No. 5,914,392, Phillip R. Hawkins, Lynn E. Murry, ANTIBODIES TO A NOVEL TISSUE INHIBITOR OF METALLOPROTEINASES, Interference No. 105,177, final judgment adverse to the patentees rendered March 11, 2004, as to claim 1.

*(Official Gazette January 18, 2005)*

Adverse Decision In Interference

Patent No. 5,914,392, Phillip R. Hawkins, Lynn E. Murry, ANTIBODIES TO A NOVEL TISSUE INHIBITOR OF METALLORPROTEINASES, Interference No. 105,177, final judgment adverse to the patentees rendered March 11, 2004, as to claim 1.

*(Official Gazette February 22, 2005)*